(12) United States Patent
Park et al.

(10) Patent No.: US 11,464,444 B2
(45) Date of Patent: Oct. 11, 2022

(54) SKIN MEASUREMENT APPARATUS AND SKIN MEASUREMENT SYSTEM COMPRISING ULTRAVIOLET RAY EMITTING DEVICE

(71) Applicant: Seoul Viosys Co., Ltd., Ansan-si (KR)

(72) Inventors: Ki Yon Park, Ansan-si (KR); Seong Tae Jang, Ansan-si (KR)

(73) Assignee: Seoul Viosys Co., Ltd., Ansan-si (KR)

( * ) Notice: Subject to any disclaimer, the term of this patent is extended or adjusted under 35 U.S.C. 154(b) by 952 days.

(21) Appl. No.: 16/240,614

(22) Filed: Jan. 4, 2019

(65) Prior Publication Data

US 2019/0133515 A1 May 9, 2019

Related U.S. Application Data

(63) Continuation of application No. PCT/KR2017/007175, filed on Jul. 5, 2017.

(30) Foreign Application Priority Data

Jul. 5, 2016 (KR) .................. 10-2016-0084973
Jul. 4, 2017 (KR) .................. 10-2017-0084953

(51) Int. Cl.
*A61B 5/00* (2006.01)
*A61N 5/06* (2006.01)
*G06V 10/143* (2022.01)

(52) U.S. Cl.
CPC ............ *A61B 5/446* (2013.01); *A61B 5/0064* (2013.01); *A61B 5/0077* (2013.01); *A61B 5/442* (2013.01);
(Continued)

(58) Field of Classification Search
CPC ..... A61B 5/446; A61B 5/0064; A61B 5/0077; A61B 5/442; G06V 10/143; A62B 5/444;
(Continued)

(56) References Cited

U.S. PATENT DOCUMENTS 7,626,153 B2 * 12/2009 Engstrand .................. G01J 1/02
250/239
7,840,064 B2 * 11/2010 Chhibber ............. G06V 10/143
382/165
(Continued)

FOREIGN PATENT DOCUMENTS

JP 2002112970 4/2002
JP 2009508648 3/2009
(Continued)

OTHER PUBLICATIONS

International Search Report dated Aug. 30, 2017 in Intl. Appl No. PCT/KR2017/007175.
(Continued)

*Primary Examiner* — Gregory M Desire
(74) *Attorney, Agent, or Firm* — H.C. Park & Associates, PLC

(57) ABSTRACT

A skin measurement apparatus for emitting a plurality of lights for photographing an image of the skin. A skin measurement apparatus includes an ultraviolet ray emitting device; a white light emitting device; a focus lens enabling incident light, which is an ultraviolet ray emitted by means of the ultraviolet ray emitting device and a white light emitted by means of the white light emitting device reflected off the skin and transmitted, to pass therethrough; and an emission control device for controlling the ultraviolet ray emitting device and the white light emitting device such that the ultraviolet ray and the white light can be emitted together. The emission control device adjusts the strength of the white light on the basis of white light control information from the outside.

20 Claims, 9 Drawing Sheets

(52) U.S. Cl.
CPC .............. *A61B 5/444* (2013.01); *A61N 5/0617* (2013.01); *A61N 2005/0661* (2013.01); *G06T 2207/30088* (2013.01); *G06V 10/143* (2022.01)

(58) Field of Classification Search
CPC .......... A61N 5/0617; A61N 2005/0661; G06T 2207/30088
See application file for complete search history.

(56) References Cited

U.S. PATENT DOCUMENTS

| | | | |
|---|---|---|---|
| 8,112,293 B2* | 2/2012 | Howell | G16H 30/20 |
| | | | 600/300 |
| 8,436,287 B2* | 5/2013 | Engstrand | G01J 1/0271 |
| | | | 362/362 |
| 8,496,695 B2 | 6/2013 | Kang et al. | |
| 9,310,293 B2* | 4/2016 | Hanyu | G01N 21/33 |
| 10,083,367 B2* | 9/2018 | Braumandl | G06V 10/10 |
| 10,621,435 B2* | 4/2020 | Bridges | H04N 5/23258 |
| 10,905,331 B2* | 2/2021 | Vilenskii | A61B 5/1455 |
| 2007/0064985 A1 | 3/2007 | Chhibber et al. | |
| 2009/0196475 A1* | 8/2009 | Demirli | G06V 40/171 |
| | | | 382/128 |
| 2016/0057325 A1 | 2/2016 | Park et al. | |
| 2017/0179469 A1 | 6/2017 | Jiang et al. | |

FOREIGN PATENT DOCUMENTS

| | | |
|---|---|---|
| KR | 10-2008-0056034 | 6/2008 |
| KR | 10-2011-0118646 | 10/2011 |
| KR | 10-2012-0140328 | 12/2012 |
| KR | 10-2016-0023441 | 3/2016 |

OTHER PUBLICATIONS

KIPO Office Action in corresponding KR 10-2017-0084953, dated Aug. 13, 2021 (English Translation).

* cited by examiner

SKIN MEASUREMENT APPARATUS AND SKIN MEASUREMENT SYSTEM COMPRISING ULTRAVIOLET RAY EMITTING DEVICE

CROSS REFERENCE TO RELATED APPLICATION

This application is a Continuation of International Patent Application No. PCT/KR2017/007175, filed on Jul. 5, 2017, and claims priority from and the benefit of Korean Patent Application No. 10-2016-0084973, filed on Jul. 5, 2016, and Korean Patent Application No. 10-2017-0084953, filed on Jul. 4, 2017, each of which is incorporated by reference for all purposes as if fully set forth herein.

BACKGROUND

Field

Exemplary embodiments of the inventive concepts relate to a skin measurement apparatus including an ultraviolet (UV) light emitting device and a skin measurement system.

DISCUSSION OF THE BACKGROUND

UV light generally refers to light in the wavelength range of 100 nm to 400 nm and has higher energy than visible light. UV light emitted from the sun is divided into ultraviolet-A, ultraviolet-B, and ultraviolet-C. It is known in the art that most UV-C is absorbed by the ozone layer and UV-A and UV-B reach the surface of the earth.

Recently, various techniques using UV light have been actively developed. Health conditions of the skin can be measured by irradiating the skin of the body with UV light to photograph the skin using the irradiated UV light. For example, UV light is emitted towards the skin through a UV filter and an image can be obtained from the light reflected from the skin such that the health conditions of the skin can be checked based on the image.

The above information disclosed in this Background section is only for understanding of the background of the inventive concepts, and, therefore, it may contain information that does not constitute prior art.

SUMMARY

Exemplary embodiments of the inventive concepts provide a skin measurement apparatus and a skin measurement system adapted to emit light in various wavelength ranges to photograph the skin.

In accordance with exemplary embodiments of the inventive concepts, a skin measurement apparatus may include: a UV light emitting device; a white light emitting device; a focus lens allowing incident light to pass therethrough, the incident light being UV light emitted from the UV light emitting device and reflected from the skin and white light emitted from the white light emitting device and reflected from the skin; and an emission control device controlling the UV light emitting device and the white light emitting device to simultaneously emit the UV light and the white light. The emission control device controls intensity of the white light based on white light control information from outside.

In one exemplary embodiment, the emission control device may control the UV light emitting device to emit the UV light at constant intensity during control of the intensity of the white light.

In one exemplary embodiment, the skin measurement apparatus may further include an interface receiving an input selecting one of a plurality of modes corresponding to different intensities of white light as the white light control information.

In one exemplary embodiment, the interface may provide a white light control signal corresponding to the selected mode, and the emission control device may include a white light controller regulating the intensity of the white light in response to the white light control signal.

In one exemplary embodiment, the white light control signal may indicate one of a current level and a current frequency.

In one exemplary embodiment, the skin measurement apparatus may further include an interface receiving the white light control information and sending a white light control signal corresponding to the intensity of the white light according to the white light control information. Here, the emission control device may include a white light controller regulating the intensity of the white light in response to the white light control signal.

In one exemplary embodiment, the skin measurement apparatus may further include: a UV sensor adapted to output sensing information by sensing UV light received from outside; and an interface operating one of the emission control device and the UV sensor in response to a first input received from outside.

In one exemplary embodiment, the interface may send the sensing information from the UV sensor through a communicator when the UV sensor is activated.

In one exemplary embodiment, the interface may receive a second input as the white light control information when the emission control device is activated.

In one exemplary embodiment, the skin measurement apparatus may further include a securing device securing a camera lens of a mobile device under the focus lens.

In one exemplary embodiment, the x and y coordinates of the UV light may be 0.3 or less and 0.2 or less, respectively, in the International Commission on Illumination (CIE) 1931 color space.

In one exemplary embodiment, the UV light may have a wavelength of 400 nm or less.

In one exemplary embodiment, the skin measurement apparatus may further include at least one optical sensor adapted to detect light reflected from the skin. The optical sensor may quantify the light reflected from the skin.

In addition, the skin measurement apparatus may include a plurality of optical sensors corresponding to the plurality of modes of the interface, respectively. Here, an optical sensor corresponding to a selected mode among the plurality of modes may detect and quantify light reflected from the skin.

In accordance with exemplary embodiments of the inventive concepts, a skin measurement apparatus includes: a UV light emitting device; a white light emitting device; a focus lens disposed in the opening and allowing incident light to pass therethrough, the incident light being UV light emitted from the UV light emitting device and reflected from the skin and white light emitted from the white light emitting device and reflected from the skin; a securing device securing a camera lens of a mobile device under the focus lens; an emission control device controlling the UV light emitting device and the white light emitting device; and a communicator sending white light control information received from the mobile device to the emission control device. The emission control device may control the white light emitting device to change intensity of the white light in response to the white light control information when the UV light is emitted at constant intensity.

In one exemplary embodiment, the skin measurement apparatus may further include an interface generating a white light control signal selecting one of a plurality of modes according to the white light control information. The emission control device may include a white light controller controlling the intensity of the white light corresponding to a selected mode in response to the white light control signal.

In one exemplary embodiment, the skin measurement apparatus may further include: a UV sensor adapted to output sensing information by sensing UV light received from outside; and an interface operating one of the emission control device and the UV sensor when a first input received from outside.

In one exemplary embodiment, the interface may receive a second input as the white light control information when the emission control device is activated.

In one exemplary embodiment, the x and y coordinates of the UV light may be 0.3 or less and 0.2 or less, respectively, in the CIE 1931 color space.

In one exemplary embodiment, the UV light may have a wavelength of 400 nm or less.

In one exemplary embodiment, the skin measurement apparatus may further include at least one optical sensor adapted to detect light reflected from the skin.

In one exemplary embodiment, the skin measurement apparatus may include a plurality of optical sensors corresponding to the plurality of modes, respectively. Here, an optical sensor corresponding to a selected mode among the plurality of modes may detect and quantify the light reflected from the skin.

In accordance with exemplary embodiments of the inventive concepts, a skin measurement system includes a skin measurement apparatus including: a UV light emitting device emitting UV light; a white light emitting device emitting white light; a focus lens allowing incident light to pass therethrough, the incident light being the UV light and the white light reflected from the skin; and an emission control device controlling the UV light emitting device and the white light emitting device. In addition, the skin measurement system may include a mobile device photographing the skin through a camera lens. The skin measurement apparatus is secured to the mobile device such that the focus lens is placed above the camera lens of the mobile device. Further, the skin measurement apparatus regulates intensity of the white light emitted from the white light emitting device.

In one exemplary embodiment, the skin measurement apparatus may further include a communicator sending white light control information received from the mobile device to the emission control device.

In one exemplary embodiment, the skin measurement apparatus may further include an interface generating a white light control signal selecting one of a plurality of modes according to the white light control information. The emission control device of the skin measurement apparatus may include a white light controller controlling the intensity of the white light in response to the white light control signal.

In one exemplary embodiment, the skin measurement apparatus may further include: a UV sensor adapted to output sensing information by sensing UV light received from outside; and an interface operating one of the emission control device and the UV sensor when a first input received from outside.

The interface may receive a second input as the white light control information when the emission control device is activated.

In one exemplary embodiment, the x and y coordinates of the UV light may be 0.3 or less and 0.2 or less, respectively, in the CIE 1931 color space.

In one exemplary embodiment, the UV light may have a wavelength of 400 nm or less.

In one exemplary embodiment, the skin measurement system may further include at least one optical sensor adapted to detect light reflected from the skin.

The optical sensor may quantify the light reflected from the skin.

In one exemplary embodiment, the skin measurement system may include a plurality of optical sensors corresponding to the plurality of modes, respectively. Here, an optical sensor corresponding to a selected mode among the plurality of modes may detect and quantify light reflected from the skin.

Exemplary embodiments of the present disclosure provide a skin measurement apparatus and a skin measurement system adapted to emit light in various wavelength ranges to photograph the skin.

BRIEF DESCRIPTION OF THE DRAWINGS

The accompanying drawings, which are included to provide a further understanding of the invention and are incorporated in and constitute a part of this specification, illustrate exemplary embodiments of the invention, and together with the description serve to explain the inventive concepts.

DETAILED DESCRIPTION

Figure 1:
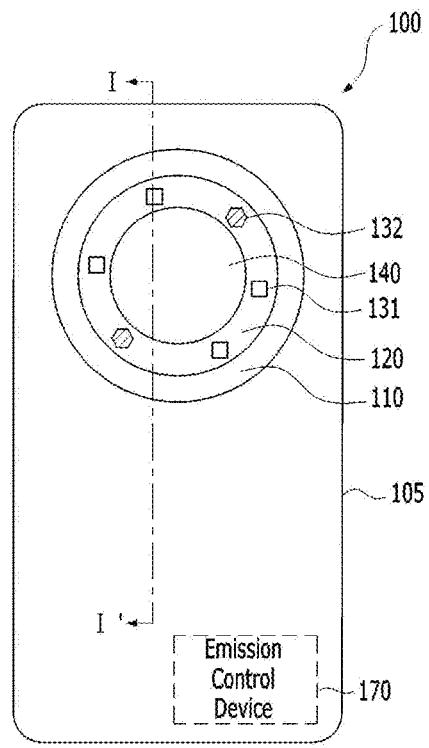
FIG. 1 is a plan view of a skin measurement apparatus according to one exemplary embodiment of the inventive concepts.

In the following description, for the purposes of explanation, numerous specific details are set forth in order to provide a thorough understanding of various exemplary embodiments or implementations of the invention. As used herein "embodiments" and "implementations" are interchangeable words that are non-limiting examples of devices or methods employing one or more of the inventive concepts disclosed herein. It is apparent, however, that various exemplary embodiments may be practiced without these specific details or with one or more equivalent arrangements. In other instances, well-known structures and devices are shown in block diagram form in order to avoid unnecessarily obscuring various exemplary embodiments. Further, various exemplary embodiments may be different, but do not have to be exclusive. For example, specific shapes, configurations, and characteristics of an exemplary embodiment may be used or implemented in another exemplary embodiment without departing from the scope of the inventive concepts.

Unless otherwise specified, the illustrated exemplary embodiments are to be understood as providing exemplary features of varying detail of some ways in which the inventive concepts may be implemented in practice. Therefore, unless otherwise specified, the features, components, modules, layers, films, panels, regions, and/or aspects, etc. (hereinafter individually or collectively referred to as "elements"), of the various embodiments may be otherwise combined, separated, interchanged, and/or rearranged without departing from the scope of the inventive concepts.

The use of cross-hatching and/or shading in the accompanying drawings is generally provided to clarify boundaries between adjacent elements. As such, neither the presence nor the absence of cross-hatching or shading conveys or indicates any preference or requirement for particular materials, material properties, dimensions, proportions, commonalities between illustrated elements, and/or any other characteristic, attribute, property, etc., of the elements, unless specified. Further, in the accompanying drawings, the size and relative sizes of elements may be exaggerated for clarity and/or descriptive purposes. When an exemplary embodiment may be implemented differently, a specific process order may be performed differently from the described order. For example, two consecutively described processes may be performed substantially at the same time or performed in an order opposite to the described order. Also, like reference numerals denote like elements.

When an element, such as a layer, is referred to as being "on," "connected to," or "coupled to" another element or layer, it may be directly on, connected to, or coupled to the other element or layer or intervening elements or layers may be present. When, however, an element or layer is referred to as being "directly on," "directly connected to," or "directly coupled to" another element or layer, there are no intervening elements or layers present. To this end, the term "connected" may refer to physical, electrical, and/or fluid connection, with or without intervening elements. Further, the D1-axis, the D2-axis, and the D3-axis are not limited to three axes of a rectangular coordinate system, such as the x, y, and z-axes, and may be interpreted in a broader sense. For example, the D1-axis, the D2-axis, and the D3-axis may be perpendicular to one another, or may represent different directions that are not perpendicular to one another. For the purposes of this disclosure, "at least one of X, Y, and Z" and "at least one selected from the group consisting of X, Y, and Z" may be construed as X only, Y only, Z only, or any combination of two or more of X, Y, and Z, such as, for instance, XYZ, XYY, YZ, and ZZ. As used herein, the term "and/or" includes any and all combinations of one or more of the associated listed items.

Although the terms "first," "second," etc. may be used herein to describe various types of elements, these elements should not be limited by these terms. These terms are used to distinguish one element from another element. Thus, a first element discussed below could be termed a second element without departing from the teachings of the disclosure.

Spatially relative terms, such as "beneath," "below," "under," "lower," "above," "upper," "over," "higher," "side" (e.g., as in "sidewall"), and the like, may be used herein for descriptive purposes, and, thereby, to describe one elements relationship to another element(s) as illustrated in the drawings. Spatially relative terms are intended to encompass different orientations of an apparatus in use, operation, and/or manufacture in addition to the orientation depicted in the drawings. For example, if the apparatus in the drawings is turned over, elements described as "below" or "beneath" other elements or features would then be oriented "above" the other elements or features. Thus, the exemplary term "below" can encompass both an orientation of above and below. Furthermore, the apparatus may be otherwise oriented (e.g., rotated 90 degrees or at other orientations), and, as such, the spatially relative descriptors used herein interpreted accordingly.

The terminology used herein is for the purpose of describing particular embodiments and is not intended to be limiting. As used herein, the singular forms, "a," "an," and "the" are intended to include the plural forms as well, unless the context clearly indicates otherwise. Moreover, the terms "comprises," "comprising," "includes," and/or "including," when used in this specification, specify the presence of stated features, integers, steps, operations, elements, components, and/or groups thereof, but do not preclude the presence or addition of one or more other features, integers, steps, operations, elements, components, and/or groups thereof. It is also noted that, as used herein, the terms "substantially," "about," and other similar terms, are used as terms of approximation and not as terms of degree, and, as such, are utilized to account for inherent deviations in measured, calculated, and/or provided values that would be recognized by one of ordinary skill in the art.

Various exemplary embodiments are described herein with reference to sectional and/or exploded illustrations that are schematic illustrations of idealized exemplary embodiments and/or intermediate structures. As such, variations from the shapes of the illustrations as a result, for example, of manufacturing techniques and/or tolerances, are to be expected. Thus, exemplary embodiments disclosed herein should not necessarily be construed as limited to the particular illustrated shapes of regions, but are to include deviations in shapes that result from, for instance, manufacturing. In this manner, regions illustrated in the drawings may be schematic in nature and the shapes of these regions may not reflect actual shapes of regions of a device and, as such, are not necessarily intended to be limiting.

As is customary in the field, some exemplary embodiments are described and illustrated in the accompanying drawings in terms of functional blocks, units, and/or modules, such as control boards and control units. Those skilled in the art will appreciate that these blocks, units, and/or modules are physically implemented by electronic (or optical) circuits, such as logic circuits, discrete components, microprocessors, hard-wired circuits, memory elements, wiring connections, and the like, which may be formed using semiconductor-based fabrication techniques or other manufacturing technologies. In the case of the blocks, units, and/or modules being implemented by microprocessors or other similar hardware, they may be programmed and controlled using software (e.g., microcode) to perform various functions discussed herein and may optionally be driven by firmware and/or software. It is also contemplated that each block, unit, and/or module may be implemented by dedicated hardware, or as a combination of dedicated hardware to perform some functions and a processor (e.g., one or more programmed microprocessors and associated circuitry) to perform other functions. Also, each block, unit, and/or module of some exemplary embodiments may be physically separated into two or more interacting and discrete blocks, units, and/or modules without departing from the scope of the inventive concepts. Further, the blocks, units, and/or modules of some exemplary embodiments may be physically combined into more complex blocks, units, and/or modules without departing from the scope of the inventive concepts.

Unless otherwise defined, all terms (including technical and scientific terms) used herein have the same meaning as commonly understood by one of ordinary skill in the art to which this disclosure is a part. Terms, such as those defined in commonly used dictionaries, should be interpreted as having a meaning that is consistent with their meaning in the context of the relevant art and should not be interpreted in an idealized or overly formal sense, unless expressly so defined herein.

FIG. 1 is a plan view of a skin measurement apparatus 100 according to one exemplary embodiment of the inventive concepts.

Referring to FIG. 1, the skin measurement apparatus 100 include a body 105, a cover 110, a support 120, at least one UV light emitting device 131, at least one white light emitting device 132, a focus lens 140, and an emission control device 170.

The cover 110 is disposed in at least some region of the body 105. The cover 110 may have a circular shape. The cover 110 may define a region in which the UV light emitting device 131, the white light emitting device 132, and the focus lens 140 are placed. The cover 110 blocks external light to prevent light emitted from the UV light emitting device 131 and the white light emitting device 132 from being disturbed by external light.

The UV light emitting device 131 and the white light emitting device 132 are arranged around the focus lens 140. The emission control device 170 is received in the body 105. The UV light emitting device 131 is adapted to emit UV light in response to control of the emission control device 170. The white light emitting device 132 is adapted to emit white light in response to control of the emission control device 170. In FIG. 1, the skin measurement apparatus 100 is illustrated as including four UV light emitting devices and two white light emitting devices. However, it should be understood that this exemplary embodiment is provided for illustration only, and the number and locations of the UV light emitting devices and the white light emitting devices for the skin measurement apparatus 100 may vary depending upon intensity and balance of light required.

Figure 2:
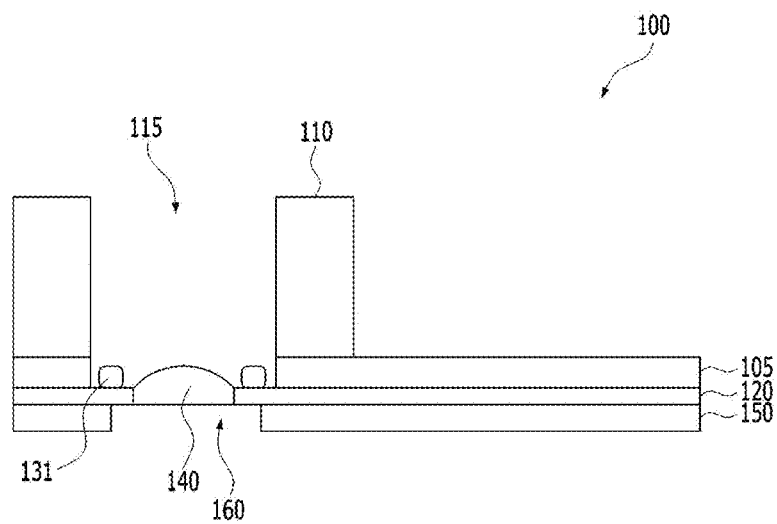
FIG. 2 is a cross-sectional view taken along line I-I' of FIG. 1.
Figure 3:
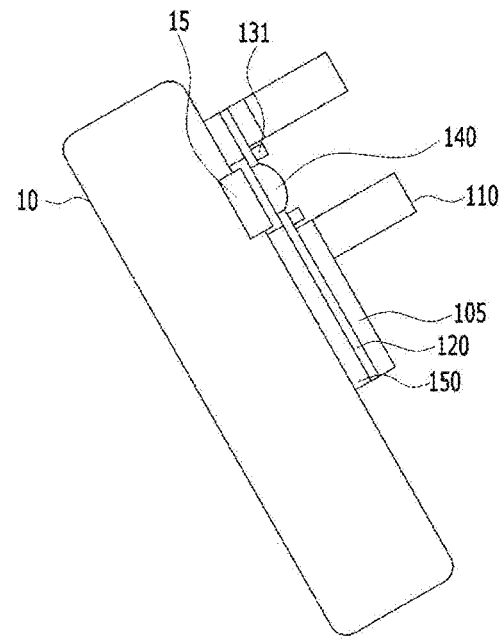
FIG. 3 is a side view of a skin measurement system.

FIG. 2 is a cross-sectional view taken along line I-I' of FIG. 1. FIG. 3 is a side view of a skin measurement system. Referring to FIG. 3, the skin measurement system is composed of a mobile device 10 and the skin measurement apparatus 100 mounted on the mobile device 10. Herein, the mobile device 10 refers to a mobile or portable terminal having a small size.

Referring to FIG. 2, the cover 110 is disposed on the body 105. The cover 110 has a predetermined height to set a focal distance between the focus lens 140 and a measurement object (for example, skin). For example, the cover 110 may provide a focal distance of 10 nm to 15 mm. For example, the cover 110 may include a component allowing the height of the cover to be adjusted in an upward/downward direction to provide a variable focal distance. In one exemplary embodiment, the cover 110 may have a cylindrical opening 115.

The support 120 is disposed on a lower surface of the body 105. The support 120 extends in a plane direction of the body 105 and may protrude towards the opening 115.

The UV light emitting device 131 and the white light emitting device 132 (see FIG. 1) are disposed on the support 120 in the opening 115. The UV light emitting device 131 and the white light emitting device 132 emit UV light and white light towards an upper portion of the skin measurement apparatus 100, respectively.

In FIG. 2, the support 120 is illustrated as a separate component from the body 105. However, it should be understood that this structure is provided for illustration only and the body 105 may be integrally formed with the support 120. For example, the body 105 may include a portion protruding towards the opening 115 to serve as the support 120.

The focus lens 140 allows incident light, which is UV light emitted from the UV light emitting device 131 and reflected from a measurement object and white light emitted from the white light emitting device 132 and reflected from the measurement object, to pass therethrough.

A securing device 150 is disposed on a lower surface of the support 120. The securing device 150 has a lens hole 160 that overlaps the opening 115. The focus lens 140 is disposed between the opening 115 and the lens hole 160. Accordingly, each of the focus lens 140 and the securing device 150 has a groove. When the skin measurement apparatus 100 is secured to the mobile device 10, as shown in FIG. 3, a camera lens 15 of the mobile device 10 is disposed under the focus lens 140, that is, in the lens hole 160.

The mobile device 10 may photograph a measurement object according to light transferred through the camera lens 15. According to this exemplary embodiment, the skin measurement apparatus 100 regulates intensity of white light emitted from the white light emitting device 132 such that the mobile device 10 can photograph skin sebum, wrinkles, pigments, black spots, sunscreen residue, acne, pores, erythema, atopy, psoriasis, skin conditions, and skin problems.

Figure 4:
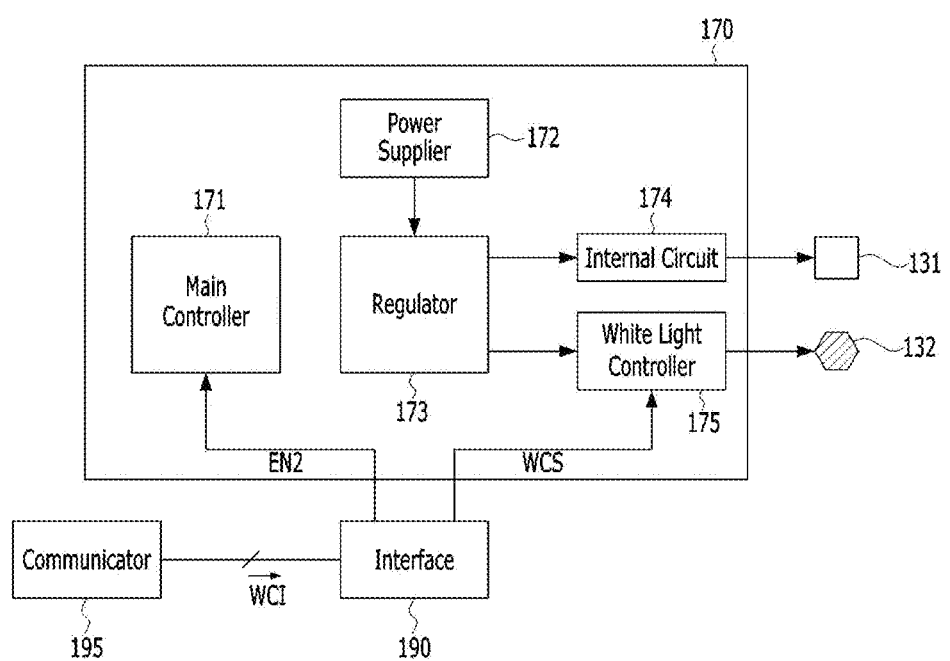
FIG. 4 is a block diagram illustrating an emission control device, an interface, and a communicator of the skin measurement apparatus according to the exemplary embodiment.

FIG. 4 is a block diagram illustrating the emission control device 170, an interface 190, and a communicator 195 of the skin measurement apparatus according to the exemplary embodiment.

Referring to FIG. 4, the emission control device 170 is connected to the UV light emitting device 131 and the white light emitting device 132. The emission control device 170 includes a main controller 171, a power supplier 172, a regulator 173, an internal circuit 174, and a white light controller 175.

The main controller 171 controls operation of the emission control device 170. The main controller 171 receives an enable signal EN from the interface 190. Upon receipt of the enable signal EN, the main controller 171 may control the components of the emission control device 170 such that the UV light emitting device 131 and the white light emitting device 132 are operated to emit light. When receipt of the enable signal EN is stopped, the main controller 171 may control the components of the emission control device 170 to stop light emission of the UV light emitting device 131 and the white light emitting device 132. For example, the main controller 171 may activate or deactivate the regulator 173 in response to the enable signal EN. Alternatively, the emission control device 170 may further include a switching element between the power supplier 172 and the regulator 173, and the main controller 171 may turn the switching element on/off in response to the enable signal EN.

The power supplier 172 is adapted to supply power to the regulator 173. For example, the power supplier 172 may be realized by a battery. Alternatively, power may be supplied from the mobile device 10 (see FIG. 2) through the communicator 195, unlike the exemplary embodiment shown in FIG. 4. In this case, power may be supplied from the mobile device 10 in a wired communication manner or a wireless communication manner.

The regulator 173 is adapted to output stable voltage through regulation of power. For example, the regulator 173 may change a voltage level of the power to a target voltage level and may output a voltage having a changed voltage level. For example, the regulator 173 is adapted to filter swing of power voltage. If the power supplied from the power supplier 172 has a target voltage, the regulator 173 may be omitted.

The internal circuit 174 receives regulated power. The internal circuit 174 controls the UV light emitting device 131 to emit UV light using the regulated power.

According to this exemplary embodiment, when white light from the white light emitting device 132 varies, the internal circuit 174 controls the UV light emitting device 131 to emit UV light at constant intensity. For example, the internal circuit 174 may supply a constant level of electric current to the UV light emitting device 131. Here, the constant level of electric current may correspond to the intensity of UV light. The UV light emitting device 131 may emit UV light depending upon the electric current supplied thereto.

In one exemplary embodiment, the intensity of UV light emitted from the UV light emitting device 131 may be changed upon change of setting of the internal circuit 174. The internal circuit 174 may supply electric current to the UV light emitting device 131 corresponding to the changed setting thereof. Such change of setting may be performed through the communicator 195 and the interface 190. For example, setting of the internal circuit 174 may be changed through the mobile device 10.

The white light controller 175 receives a regulated voltage. The white light controller 175 controls the white light emitting device 132 to emit white light using the regulated voltage.

According to this exemplary embodiment, the white light controller 175 receives a white light control signal WCS from the interface 190. When the UV light emitting device 131 emits UV light at constant intensity, the white light controller 175 may change the white light emitted from the white light emitting device 132 in response to the white light control signal WCS. In one exemplary embodiment, the white light controller 175 may change the white light by regulating the level of electric current supplied to the white light emitting device 132 in response to the white light control signal WCS. In one exemplary embodiment, the white light controller 175 supplies electric current to the white light emitting device 132 at a certain frequency while changing the frequency of electric current in response to the white light control signal WCS, thereby enabling variation of white light. Further, the white light controller 175 may regulate the white light emitted from the white light emitting device 132 through one of various methods.

In one exemplary embodiment, the white light control signal WCS may indicate one of the level and frequency of electric current. In one exemplary embodiment, the white light control signal WCS may be provided as a digital value or an analog value.

The interface 190 interfaces between the emission control device 170 and the communicator 195. The interface 190 transfers the enable signal EN received from the communicator 195 to the main controller 171. That is, activation or deactivation of light emission may be selected through the mobile device 10.

The interface 190 receives white light control information WCI from the communicator 195 and outputs a white light control signal WCS according to the white light control information WCI. The white light control information WCI includes information about the intensity of white light.

In one exemplary embodiment, the white light control information WCI may be an input selecting one of a plurality of modes. The plural modes may correspond to intensities of white light. For example, first to $n^{th}$ modes correspond to sequentially increasing intensities of white light and the white light control information WCI may be an input selecting one of the first to $n^{th}$ modes.

In one exemplary embodiment, the skin measurement apparatus 100 may send a trigger signal to the mobile device 10 through the communicator 195 upon emission of UV light or white light according to the white light control information WCI. The transmitted trigger signal may trigger the mobile device 10 to photograph an image. The mobile device 10 may photograph a measurement object using light transferred through the camera lens 15 in response to a trigger signal.

The communicator 195 communicates with the mobile device 10. The communicator 195 may communicate with the mobile device 10 in at least one manner of wired communication and wireless communication.

When the communicator 195 adopts a wireless communication scheme, the communicator 195 is configured to perform wireless communication with the mobile device 10 placed near the communicator using at least one protocol selected from among near field communication (NFC), Bluetooth communication, Wi-Fi communication, LTE D2D (Device-to-Device) communication, RFID (Radio Frequency Identification) communication, magnetic secure transmission communication, Zigbee communication, IrDA (infrared Data Association) communication, ultra-wide band (UWB) UWB, Ant+ UWB, and other suitable wireless communication schemes.

When the communicator 195 adopts a wired communication scheme, the communicator 195 is configured to perform wired communication with the mobile device 10 using at least one protocol selected from among a universal serial bus (USB) protocol, a multimedia card (MMC) protocol, a small computer small interface (SCSI) protocol, an enhanced small disk interface (ESDI) protocol, and other suitable wired communication schemes.

The interface 190 and the communicator 195 may be mounted on the body 105. The interface 190 and the communicator 195 may be operated by power from the power supplier 172.

In one exemplary embodiment, at least one of the emission control device 170, the interface 190, and the communicator 195 may be included in a single integrated circuit. For example, all of the emission control device 170, the interface 190, and the communicator 195 may be provided to a single integrated circuit to reduce an occupation area in the skin measurement apparatus.

Figure 5:
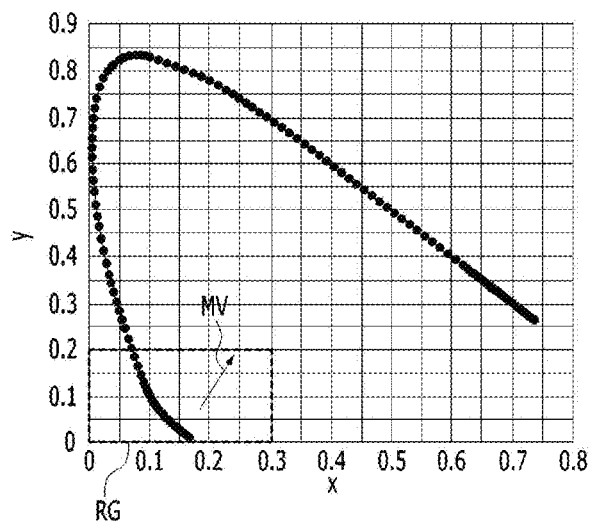
FIG. 5 is a graph depicting the CIE 1931 color space.

FIG. 5 is a graph depicting the CIE 1931 color space. In FIG. 5, the axis of abscissa indicates an x-coordinate in CIE and the axis of ordinate indicates a y-coordinate in CIE. In CIE, the z-coordinate may be calculated by 1−(x+y).

Referring to FIG. 5, a range RG is shown. The range RG indicates that an x-coordinate value is 0.3 or less and a y-coordinate value is 0.2 or less.

Even upon regulation of white light emitted from the white light emitting device 132 (see FIG. 4), use of UV light in which the x-coordinate value exceeds 0.3 and the y-coordinate value exceeds 0.2 makes it difficult for mixed light of the white light and the UV light to move in the color space due to a white light component included in the UV light. In this case, it is difficult for the mobile device to photograph an image in various modes.

According to this exemplary embodiment, the UV light emitted from the UV light emitting device 131 (see FIG. 4) may have one value selected from various values within the range RG.

According to another exemplary embodiment, the UV light emitted from the UV light emitting device 131 may have a wavelength of 400 nm or less. The UV light emitted from the UV light emitting device 131 may have a wavelength near blue light.

Figure 6:
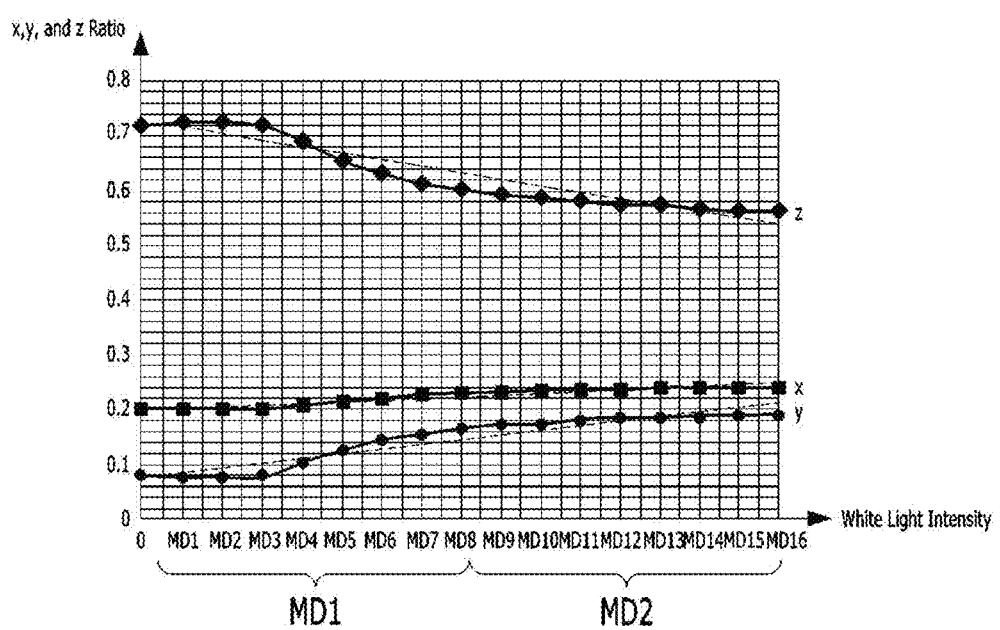
FIG. 6 is a graph depicting x, y and z-coordinates of mixed light according to a plurality of modes.

FIG. 6 is a graph depicting x, y and z-coordinates of mixed light according to a plurality of modes. In first to sixteenth modes MD1 to MD16, UV light emitted from the UV light emitting device 131 (see FIG. 4) has constant intensity and white light emitted from the white light emitting device 132 (see FIG. 4) has gradually increasing intensity. The graph of FIG. 6 is obtained from optical fibers disposed in a region corresponding to the focus lens 140.

Referring to FIG. 6, the x, y and z-coordinates are substantially linearly changed with increasing intensity of the white light. As the intensity of the white light increases, the x and y-coordinates increase, whereas the z-coordinate decreases. For example, the x-coordinate may be represented by a function of 0.0033 m+0.1966 and the y-coordinate may be represented by a function 0.0086*m+0.0761, and the z-coordinate may be represented by a function of −0.0119*m+0.7273 (m indicating a mode) according to mode. The functions of the x-, y and z-coordinates are represented by dotted lines.

Linear variation of the color coordinates of the mixed light means variation of the color coordinates of incident light provided through reflection of the mixed light by the skin. Accordingly, an image photographed by the mobile device 10 may be changed in the first to sixteenth modes MD1 to MD16. Referring to FIG. 5, movement MV of the x and y-coordinates of the mixed light upon increase in intensity of white light is shown. The movement MV shows that the color of the mixed light is moved towards white light in the CIE 1931 color space.

In one exemplary embodiment, since the color coordinates of the mixed light are linearly moved in each of the modes MD1 to MD16, the mobile device 10 may photograph skin sebum, wrinkles, pigments, black spots, sunscreen residue, acne, pores, erythema, atopy, psoriasis, skin conditions, and skin problems.

It should be understood that the number of modes MD1 to MD16 is not limited to a particular value. For example, two modes MD1 and MD2 may be provided. In a first mode MD1, one of skin sebum, wrinkles, pigments, black spots, and sunscreen residue may be photographed, and in a second mode MD2, one of acne, pores, erythema, atopy, and psoriasis may be photographed.

Information relating to an object to be photographed in a certain mode may be supplied to a user through an application installed in the mobile device 10. Then, the user may confirm a photographed image by selecting one of the first and second modes MD1, MD2.

In a structure wherein UV light emitting devices adapted to emit UV light with various wavelengths are mounted on the skin measurement apparatus 100, the skin may be photographed at various wavelengths. However, this structure increases manufacturing costs of the skin measurement apparatus 100. Conversely, the skin measurement apparatus 100 according to this exemplary embodiment includes the UV light emitting device 131 adapted to emit UV light and the white light emitting device 132 adapted to emit white light, in which the intensity of white light is regulated based on the white light control information sent from the outside. As a result, mixed light may have various wavelengths. Accordingly, the skin measurement apparatus 100 may be manufactured at reduced costs while enabling image photographing at various wavelengths.

The skin measurement apparatus 100 according to this exemplary embodiment communicates with the mobile device 10 through the interface 190 (see FIG. 4) and the communicator 195 (see FIG. 4). Accordingly, the skin measurement apparatus 100 enables image photographing at various wavelengths even without components such as a display apparatus, a camera, and the like. Accordingly, the skin measurement apparatus 100 may be manufactured at reduced costs while securing improved extensive use.

Figure 7:
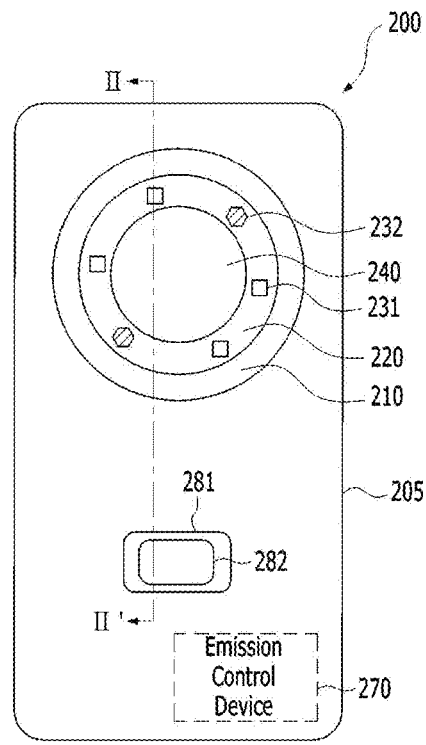
FIG. 7 is a plan view of a skin measurement apparatus according to another exemplary embodiment.
Figure 8:
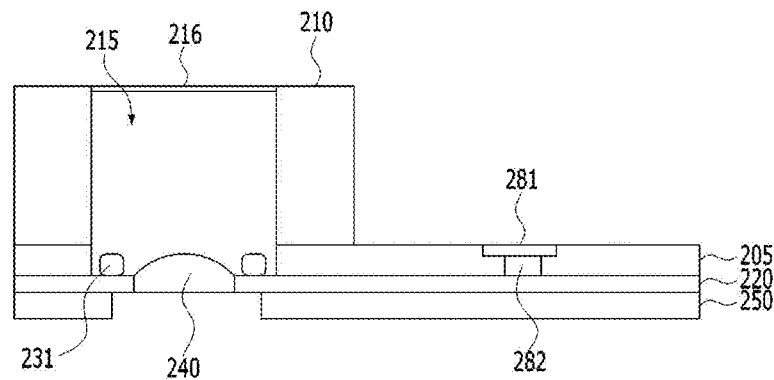
FIG. 8 is a cross-sectional view taken along line II-II' of FIG. 1.

FIG. 7 is a plan view of a skin measurement apparatus 200 according to another exemplary embodiment. FIG. 8 is a cross-sectional view taken along line II-II' of FIG. 1.

Referring to FIG. 7 and FIG. 8, the skin measurement apparatus 200 may include a body 205, a cover 210, a support 220, at least one UV light emitting device 231, at least one white light emitting device 232, a focus lens 240, a securing device 250, an emission control device 270, a UV sensor window 281, and a UV sensor 282.

The body 205, the cover 210, the support 220, the at least one UV light emitting device 231, the at least one white light emitting device 232, the focus lens 240, the securing device 250, and the emission control device 270 have the same structures as the body 105, the cover 110, the support 120, the at least one UV light emitting device 131, the at least one white light emitting device 132, the focus lens 140, the securing device 150, and the emission control device 170 described with reference to FIG. 1 and FIG. 2. Repeated description of these components will be omitted herein.

The UV sensor 282 may be mounted on the body 205 in a region outside the cover 210. The UV sensor window 281 is disposed on the UV sensor 282. The UV sensor window 281 may be formed of a material that allows UV light to effectively pass therethrough. For example, the UV sensor window 281 may be formed of quartz. The UV sensor 282 is adapted to sense the intensity of UV light.

The skin measurement apparatus 200 may further include a cover window 216. The cover window 216 covers an opening 215 to protect the UV light emitting device 231, the white light emitting device 232, and the focus lens 240 from external contaminants. For example, the cover window 216 may be formed of quartz, sapphire, and the like.

A skin measurement system may be composed of the skin measurement apparatus 200 and the mobile device 10 shown in FIG. 3. The skin measurement system may supply power and various control signals to the skin measurement apparatus 200 through the mobile device 10 (see FIG. 3).

Figure 9:
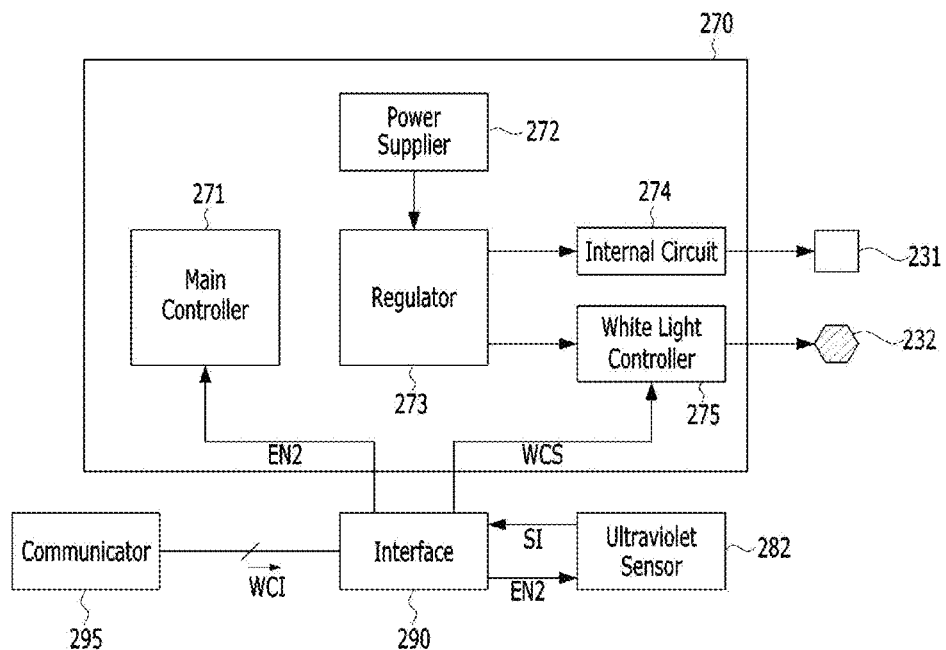
FIG. 9 is a block diagram illustrating an emission control device, an interface, and a communicator of the skin measurement apparatus according to another exemplary embodiment.
Figure 10:
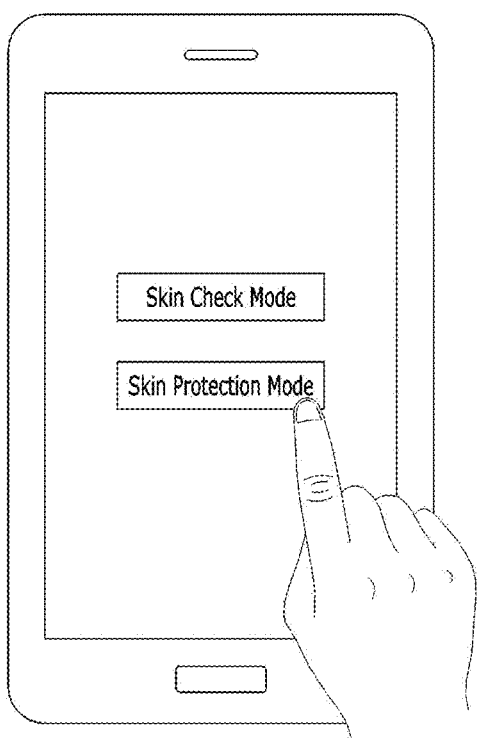
FIG. 10 shows a mobile device on which a skin check mode and a skin protection mode are displayed.

FIG. 9 is a block diagram illustrating the emission control device 270, the UV sensor 282, the interface 290, and the communicator 295 of the skin measurement apparatus according to this exemplary embodiment. FIG. 10 shows a mobile device on which a skin check mode and a skin protection mode are displayed.

Referring to FIG. 9, the emission control device 270 includes a main controller 271, a power supplier 272, a regulator 273, an internal circuit 274, and a white light controller 275. The emission control device 270 has the same structure as the emission control device 170 described with reference to FIG. 4. A repeated description thereof will be omitted herein.

The UV sensor 282 is connected to the interface 290. The UV sensor 282 may be activated in response to a first enable signal EN1. The UV sensor 282 senses the intensity of UV light to measure a UV index. In addition, the UV sensor 282 may measure a time for which the skin is exposed to UV light. The index of UV light and the measured time may correspond to a degree of UV exposure by which a user is exposed to UV light. The index of UV light and the measured time may be sent to as sensing information SI to the mobile device 10 (see FIG. 3) through the interface 290 and the communicator 295. In some exemplary embodiments, the UV sensor 282 senses at least part of UV light in the UV-B wavelength band. In other exemplary embodiments, the UV sensor 282 senses at least part of UV light in the UV B wavelength band and the UV-A wavelength band.

For example, an application installed in the mobile device 10 allows the mobile device 10 to display various pieces of information based on the sensing information (SI), for example, information on the amount of vitamin D3 produced due to absorption of UV light by the skin, a time for induction of erythema caused by UV light, and the like. Alternatively, the UV sensor 282 may further include a module for additionally generating such information. Then, the generated information may be sent to the mobile device 10 through the interface 290 and the communicator 295. The mobile device 10 receives and displays the information.

The interface 290 is connected between the emission control device 270, the UV sensor 282, and the communicator 295. The interface 290 receives one of first and second enable signals EN1, EN2 in response to a first input received through the communicator 295. For example, as shown in FIG. 10, when one of the skin check mode and the skin protection mode is selected by a user, the mobile device 10 may supply information instructing user selection as the first input to the communicator 295.

Upon receipt of the first enable signal EN1, the UV sensor 282 may be activated to sense UV light.

Upon receipt of the second enable signal EN2, the emission control device 270 is activated to emit UV light and white light, as described with reference to FIG. 4. When the emission control device 270 is activated, the interface 290 may receive a second input selecting one of the plurality of modes MD1 to MD16 (see FIG. 6) as white light control information WCI.

The skin measurement apparatus according to this exemplary embodiment includes the UV light emitting device adapted to emit UV light and the white light emitting device adapted to emit white light, in which the intensity of the white light is regulated based on the white light control information sent from the outside. Accordingly, the skin measurement apparatus may be manufactured at reduced costs while enabling image photographing at various wavelengths.

Figure 11:
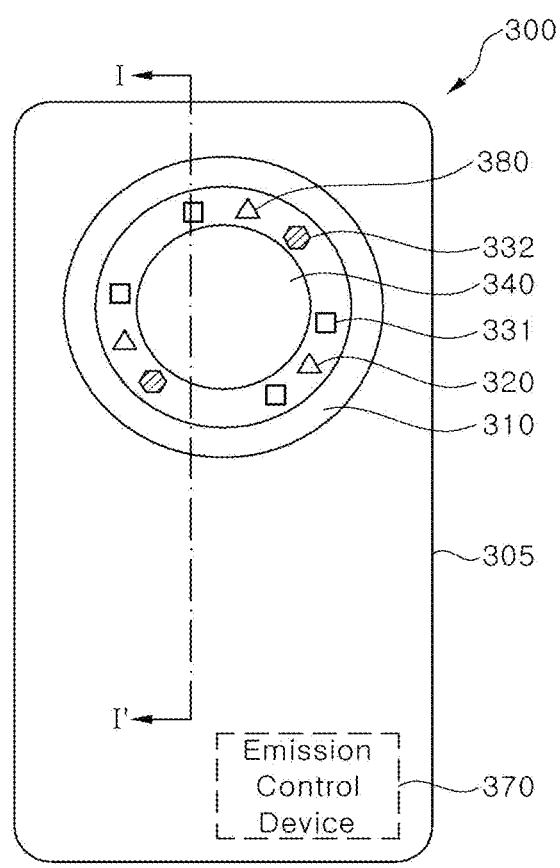
FIG. 11 is a plan view of a skin measurement apparatus according to a further exemplary embodiment.

FIG. 11 is a plan view of a skin measurement apparatus according to a further exemplary embodiment.

Referring to FIG. 11, a skin measurement apparatus 300 according to this exemplary embodiment includes a body 305, a cover 310, a support 320, at least one UV light emitting device 331, at least one white light emitting device 332, a focus lens 340, a securing device, an emission control device 370, and an optical sensor 380.

Here, descriptions of the body 305, the cover 310, the support 320, the UV light emitting device 331, the white light emitting device 332, the focus lens 340, the securing device and the emission control device 370 refer to the body 105, the cover 110, the support 120, the UV light emitting device 131, the white light emitting device 132, the focus lens 140, the securing device 150, and the emission control device 170 shown in FIG. 1 and FIG. 2.

The skin measurement apparatus 300 includes the optical sensor 380. Referring to FIG. 11, the optical sensor 380 is disposed around the focus lens 340. However, it should be understood that the present disclosure is not limited thereto and the optical sensor 380 may be placed at any location at which the optical sensor 380 can sense light reflected from the skin.

The optical sensor 380 senses light reflected from the skin. The optical sensor 380 may be a sensor adapted to sense at least one of UV light and visible light. The optical sensor 380 may quantify the amount of sensed light.

When the skin is irradiated with UV light, sunscreen on the skin reflects light. In addition, sebum reflects UV light through excitation of the UV light into a green color and a yellow color. Further, acne germs reflect UV light through excitation of the UV light into a red color.

Accordingly, not only can the skin measurement apparatus 300 photograph the skin through photographing, but also can determine skin conditions through detection and quantification of reflected light through the optical sensor 380.

For example, the optical sensor 380 may be a sensor adapted to sense UV light. In this example, the skin measurement apparatus 300 may sense and quantify the amount of sunscreen remaining on the skin through the optical sensor 380.

Alternatively, the optical sensor 380 may be a sensor adapted to sense green light. In this example, the skin measurement apparatus 300 may sense and quantify the amount of sebum of the skin through the optical sensor 380. The skin measurement apparatus 300 may determine whether the skin is a dry skin or an oily skin. Further, the skin measurement apparatus 300 may determine the degree of aging of pores or the skin based on color variation around the sebum of the skin.

The optical sensor 380 may be a sensor adapted to sense red light. In this case, the skin measurement apparatus 300 may sense acne germs through the optical sensor 380 and may quantify the spread of acne germs on the skin.

Further, the skin measurement apparatus 300 may classify a skin color type through the optical sensor 380. The degree of reflecting UV light differs depending upon skin color. Accordingly, the skin measurement apparatus 300 may determine the skin color type through quantification of the amount of UV light absorbed by or reflected from the skin through the optical sensor 380.

As such, the skin color type determined through the optical sensor 380 may be used as a standard for a user using the skin measurement apparatus 300 to determine a UV exposure time securing user safety and a suitable sun protection factor of sunscreen depending upon the skin color type.

Alternatively, the skin measurement apparatus 300 may previously store information about UV exposure times and suitable sun protection factors of sunscreens depending upon the skin color type. In this case, the skin measurement apparatus 300 may measure the skin color type and may automatically display information about the UV exposure times and the suitable sun protection factors of sunscreens depending upon the skin color type through a mobile device to be visibly confirmed by a user. Furthermore, the skin measurement apparatus 300 may be used to determine a recommended personal allowance of vitamin D depending on the skin color type or the amount of UV light reflected from the skin.

The skin measurement apparatus 300 according to this exemplary embodiment may include one of a UV light detection sensor, a green light detection sensor, a red light detection sensor, and other color detection sensors.

Alternatively, the skin measurement apparatus 300 may include at least two of the UV light detection sensor, the green light detection sensor, the red light detection sensor, and other color detection sensors.

Alternatively, the skin measurement apparatus 300 may include all of the UV light detection sensor, the green light detection sensor, the red light detection sensor, and other color detection sensors.

Figure 12:
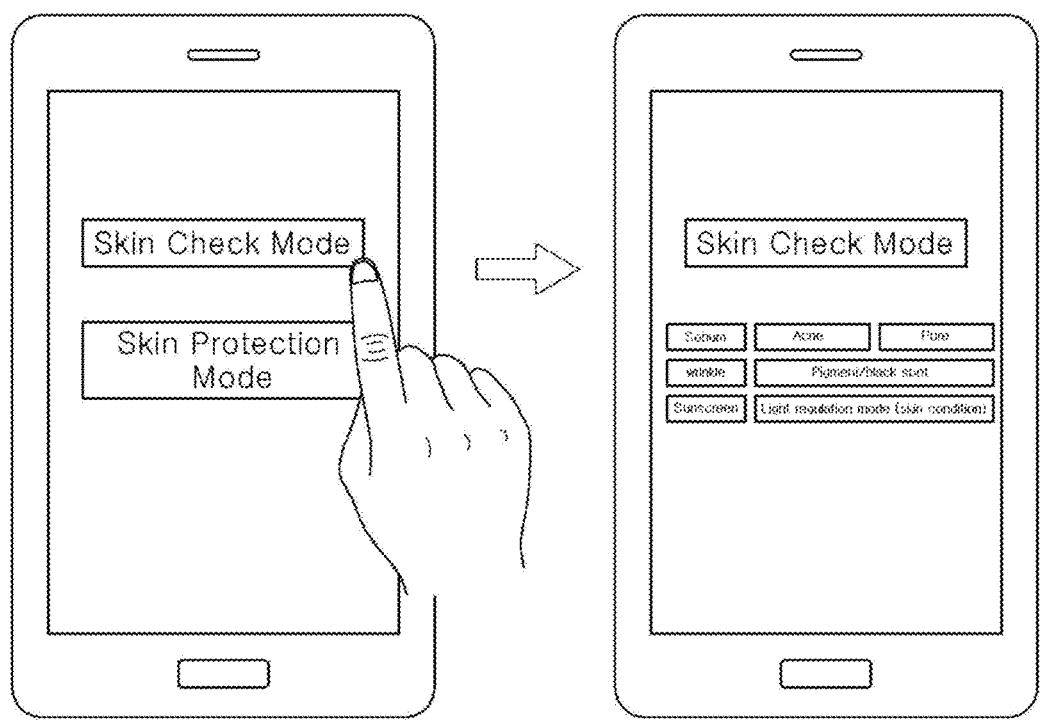
FIG. 12 is a plan view of a modification of the skin measurement apparatus shown in FIG. 11.

FIG. 12 is a plan view of a modification of the skin measurement apparatus shown in FIG. 11.

The skin measurement apparatus 300 may include at least two light detection sensors. For example, the skin measurement apparatus 300 may include a UV light detection sensor, a green light detection sensor, and a red light detection sensor.

In addition, for the skin measurement apparatus 300, various skin check modes may be provided depending upon the plural optical sensors 380. Specifically, as shown in FIG. 12, the skin measurement apparatus 300 allows a user to select various skin check modes for checking sebum, acne, pores, wrinkles, sunscreen, pigment/black spot, and the like. Here, the skin check modes are the skin check modes of the interface 290 described with reference to the block diagram of FIG. 9. In this exemplary embodiment, the skin check modes are connected to the optical sensors 380. That is, when one of the skin check modes is selected, the optical sensor 380 connected to the corresponding skin check mode may sense and quantify light reflected from the skin.

For example, upon checking sunscreen remaining on the skin, a sunscreen mode is selected such that an optical sensor adapted to sense UV light can sense and quantify light reflected from the skin.

In this way, the skin measurement apparatus 300 according to this exemplary embodiment can measure various skin conditions through various optical sensors 380.

A skin measurement system may be composed of the skin measurement apparatus 300 and the mobile device 10 shown in FIG. 3. The skin measurement system may supply power and various control signals to the skin measurement apparatus 300 through the mobile device 10 (see FIG. 3).

Figure 13:
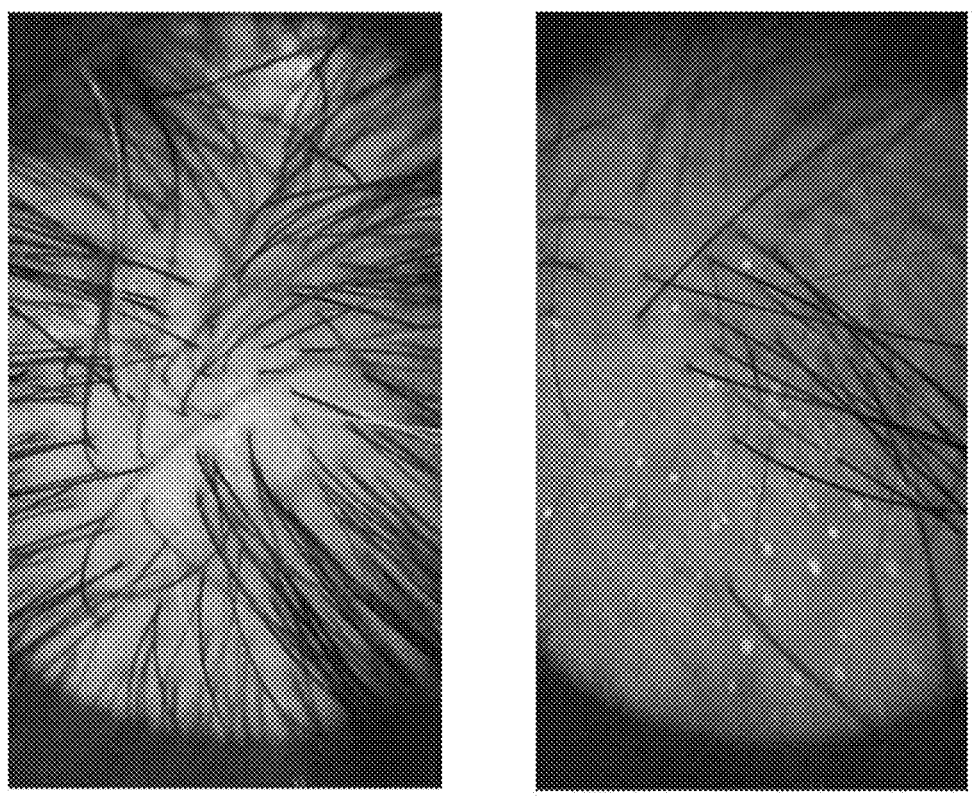
FIG. 13 and FIG. 14 illustrate a method of determining skin aging using the skin measurement apparatus shown in FIG. 11.
Figure 14:
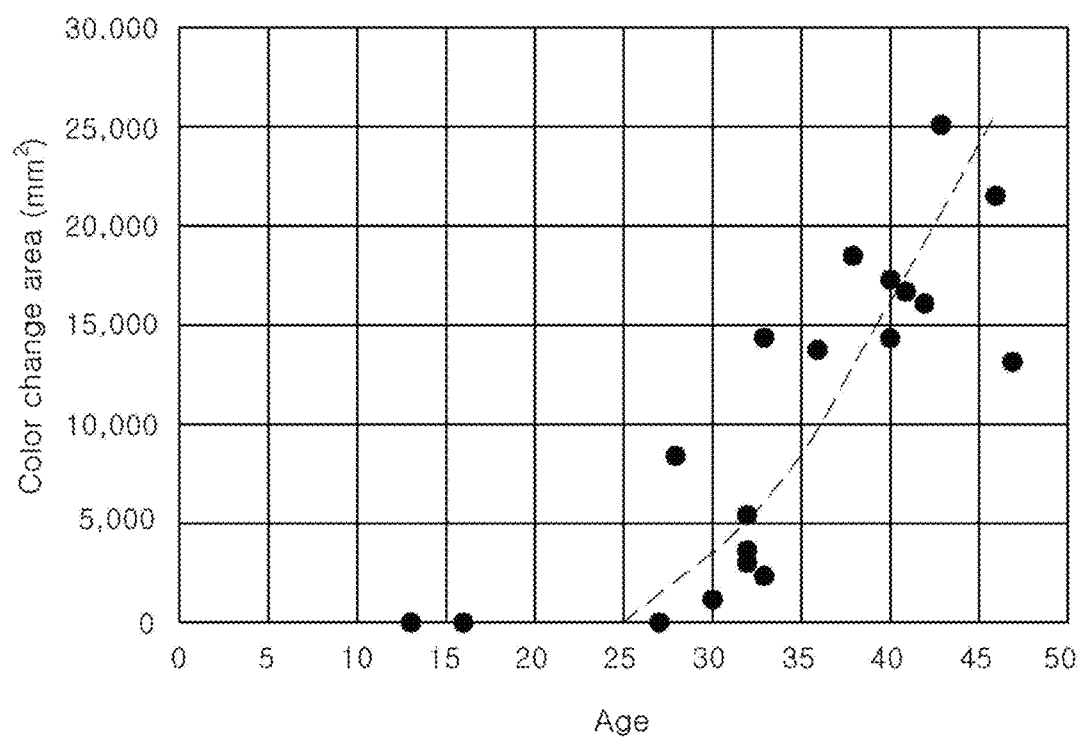

FIG. 13 and FIG. 14 illustrate a method of determining skin aging using the skin measurement apparatus shown in FIG. 11.

FIG. 13 shows images of the scalp photographed using the skin measurement apparatus 300. The left side is a photograph of a healthy scalp and the right side is a photograph of a scalp suffering from hair loss due to aging.

Comparing the healthy scalp with the scalp suffering from hair loss, it can be seen from the photograph of the scalp suffering from hair loss that a portion having a different color from the scalp occupies a large area. That is, the photograph of the scalp suffering from hair loss shows that the scalp suffering from hair loss has more areas of a different color around skin pores of the scalp from the scalp than the healthy scalp. UV light or mixed light of UV light and white light radiated to the skin is excited and reflected by sebum and appears in a different color from the scalp.

That is, it can be seen that the scalp suffering from hair loss has a larger amount of sebum and larger pieces of sebum than the healthy scalp.

In this way, the skin measurement apparatus 300 may quantify the amount of light reflected from the skin or the area of portions having a different color from the skin by photographing the skin through the optical sensor 380.

FIG. 14 is a graph depicting a color change area of the skin according to age. Here, the color change area refers to a quantified value of a portion having a different color around skin pores from healthy skin pores through the skin measurement apparatus 300. Here, the healthy skin pores may be healthy skin pores of persons in their twenties. In addition, the healthy skin pores may be healthy skin pores of a user.

In addition, the skin measurement apparatus 300 may determine the degree of aging by comparing the quantified value with a preset reference value. Herein, the reference value may be previously set as a color change area of healthy skin pores in the skin measurement apparatus 300.

Referring to FIG. 14, it can be seen that the color change area generally increases along a dotted line according to age. The dotted line is an average value of color change areas according to age. That is, the dotted line is an average value of color change areas around the healthy skin pores or in a predetermined range on the overall skin. Here, the color change area refers to an area of a portion having a different color from the skin when the skin or the scalp is photographed through the skin measurement apparatus 300. That is, the color change area is a quantified value of the amount of sebum on the skin sensed through the optical sensor 380 of the skin measurement apparatus 300.

According to the exemplary embodiments of the inventive concepts, the skin of a subject is photographed to calculate the color change area through the skin measurement apparatus 300 including the optical sensor 380. In addition, the skin measurement apparatus 300 may determinate the degree of skin aging based on a calculated color change area and the graph depicting the color change areas according to age. The degree of skin aging can be used as a reference for determination of a skin care method.

Although some exemplary embodiments have been described herein, it should be understood that these exemplary embodiments are provided for illustration only and are not to be construed in any way as limiting the inventive concepts of the present disclosure, and that various modifications, changes, alterations, and equivalent exemplary embodiments can be made by those skilled in the art.

Accordingly, the inventive concepts are not limited to such exemplary embodiments, but rather to the broader scope of the presented claims and various obvious modifications and equivalent arrangements.

The invention claimed is:

1. A skin measurement apparatus comprising:
an ultraviolet (UV) light emitting device;
a white light emitting device;
a focus lens configured to allow incident light to pass therethrough, the incident light being UV light emitted from the UV light emitting device and reflected from skin and white light emitted from the white light emitting device and reflected from the skin;
an emission control device configured to control the UV light emitting device and the white light emitting device to simultaneously emit the UV light and the white light; and an interface configured to receive white light control information and send a white light control signal corresponding to the intensity of the white light according to the white light control information, wherein the emission control device is configured to control intensity of the white light based on white light control information from outside, wherein the emission control device is configured to control the UV light emitting device to emit the UV light at constant intensity during control of the intensity of the white light, and wherein the emission control device comprises a white light controller configured to regulate the intensity of the white light in response to the white light control signal.

2. The skin measurement apparatus according to claim 1, further comprising:

an interface configured to receive an input selecting one of a plurality of modes corresponding to different intensities of white light as the white light control information, wherein the interface is configured to provide a white light control signal corresponding to the selected mode, and the emission control device comprises a white light controller configured to regulate the intensity of the white light in response to the white light control signal.

3. The skin measurement apparatus according to claim 2, wherein the white light control signal indicates one of a current level and a current frequency.

4. The skin measurement apparatus according to claim 1, further comprising:

a UV sensor configured to output sensing information by sensing UV light received from outside; and an interface configured to operate one of the emission control device and the UV sensor when a first input received from outside.

5. The skin measurement apparatus according to claim 4, wherein the interface is configured to send the sensing information from the UV sensor through a communicator when the UV sensor is activated, and the interface is configured to receive a second input as the white light control information when the emission control device is activated.

6. The skin measurement apparatus according to claim 1, wherein the x and y coordinates of the UV light are 0.3 or less and 0.2 or less, respectively, in International Commission on Illumination (CIE) 1931 color space.

7. The skin measurement apparatus according to claim 1, further comprising:

an optical sensor configured to detect light reflected from the skin, wherein the optical sensor is configured to quantify the light reflected from the skin.

8. The skin measurement apparatus according to claim 7, further comprising:

an interface configured to receive an input selecting one of a plurality of modes corresponding to different intensities of white light as the white light control information.

9. The skin measurement apparatus according to claim 8, further comprising:

a plurality of optical sensors corresponding to the plurality of modes, respectively, wherein an optical sensor corresponding to a selected mode among the plurality of modes is configured to detect and quantify the light reflected from the skin.

10. A skin measurement apparatus comprising:

an ultraviolet (UV) light emitting device;

a white light emitting device;

a focus lens configured to allow incident light to pass therethrough, the incident light being UV light emitted from the UV light emitting device and reflected from skin and white light emitted from the white light emitting device and reflected from the skin;

a securing device configured to secure a camera lens of a mobile device under the focus lens;

an emission control device configured to control the UV light emitting device and the white light emitting device; and a communicator configured to send white light control information received from the mobile device to the emission control device, wherein the emission control device is configured to control the white light emitting device to change intensity of the white light in response to the white light control information when the UV light is emitted at constant intensity.

11. The skin measurement apparatus according to claim 10, further comprising:

an interface configured to generate a white light control signal selecting one of a plurality of modes according to the white light control information, wherein the emission control device comprises a white light controller configured to control the intensity of the white light corresponding to a selected mode in response to the white light control signal.

12. The skin measurement apparatus according to claim 11, further comprising:

an optical sensor configured to detect light reflected from the skin, wherein the optical sensor configured to quantify the light reflected from the skin.

13. The skin measurement apparatus according to claim 12, further comprising:

a plurality of optical sensors corresponding to the plurality of modes, respectively, wherein an optical sensor corresponding to a selected mode among the plurality of modes is configured to detect and quantify the light reflected from the skin.

14. The skin measurement apparatus according to claim 10, further comprising:

a UV sensor configured to output sensing information by sensing UV light received from outside; and an interface configured to operate one of the emission control device and the UV sensor when a first input received from outside, wherein the interface is configured to receive a second input as the white light control information when the emission control device is activated.

15. The skin measurement apparatus according to claim 10, wherein the x and y coordinates of the UV light may be 0.3 or less and 0.2 or less, respectively, in International Commission on Illumination (CIE) 1931 color space.

16. A skin measurement system comprising:

a skin measurement apparatus, the skin measurement apparatus comprising:

an ultraviolet (UV) light emitting device configured to emit UV light;

a white light emitting device configured to emit white light;

a focus lens configured to allow incident light to pass therethrough, the incident light being the UV light and the white light reflected from the skin; and an emission control device configured to control the UV light emitting device and the white light emitting device;

a mobile device configured to photograph the skin through a camera lens; and a communicator configured to send white light control information received from the mobile device to the emission control device, wherein the skin measurement apparatus is configured to be secured to the mobile device such that the focus lens is placed above the camera lens of the mobile device, and the skin measurement apparatus is configured to regulate intensity of the white light emitted from the white light emitting device.

17. The skin measurement system according to claim 16, further comprising:

an interface configured to generate a white light control signal selecting one of a plurality of modes according to the white light control information, wherein the emission control device of the skin measurement apparatus comprises a white light controller configured to control the intensity of the white light in response to the white light control signal.

18. The skin measurement system according to claim 17, further comprising:

an optical sensor configured to detect light reflected from the skin, wherein the optical sensor is configured to quantify the light reflected from the skin.

19. The skin measurement system according to claim 16, wherein the skin measurement apparatus further comprises:

a UV sensor configured to output sensing information by sensing UV light received from outside; and an interface configured to operate one of the emission control device and the UV sensor when a first input received from outside, wherein the interface is configured to receive a second input as the white light control information when the emission control device is activated.

20. The skin measurement system according to claim 16, wherein the x and y coordinates of the UV light may be 0.3 or less and 0.2 or less, respectively, in International Commission on Illumination (CIE) 1931 color space.

* * * * *